United States Patent [19]

Patel et al.

[11] Patent Number: 5,444,087
[45] Date of Patent: Aug. 22, 1995

[54] MANUMYCIN COMPOUNDS

[75] Inventors: Pramathesh S. Patel, Ringoes, N.J.; Yue-Zhong Shu, Cheshire, Conn.

[73] Assignee: Bristol-Myers Squibb Company, Princeton, N.J.

[21] Appl. No.: 139,231

[22] Filed: Oct. 19, 1993

[51] Int. Cl.⁶ .................. C07D 303/14; C07D 303/32; A01N 43/20; A01N 31/06
[52] U.S. Cl. ..................... 514/475; 435/126; 435/127; 435/128; 435/253.5; 549/546
[58] Field of Search .................. 549/546; 514/475

[56] References Cited

U.S. PATENT DOCUMENTS

| | | | |
|---|---|---|---|
| 4,226,879 | 10/1980 | Omura et al. | 549/546 |
| 4,595,770 | 6/1986 | Brodasky et al. | 549/546 |
| 5,106,868 | 4/1992 | Nakano et al. | 514/475 |
| 5,114,967 | 5/1992 | Franco et al. | 549/546 |

OTHER PUBLICATIONS

Hara, Mitsunobu et al., "Identification of Ras Farnesyltransferase Inhibitors By Microbial Screening"; Proc. Natl. Acad. Sci, USA, vol. 90, pp. 2281–2285 (Mar., 1993).
Zeeck et al., "The Structure of Manumycin I. Characterization, Structure Elucidation and Biological Activity.", The Journal of Antibiotics, vol. XL, No. 11, pp. 1530–1540 (Nov. 1987).
Zeeck, et al., "The Structure of Manumycin II. Derivatives", The Journal of Antibiotics, vol. XL, No. 11, pp. 1541–1548 (Nov. 1987).
Zeeck et al., "Directed Biosynthesis as An Alternative to Synthetic Modifications of Antibiotics", Antibiotics and Antiviral Compounds, Chemical Synthesis and Modification, pp. 75–87 (1993).
Kakinuma et al., "The Structure of Asukamycin, A Possible Shunt Metabolite from 3-Dehydroquinic Acid in the Shikimate Pathway," Journal of the American Chemical Society, vol. 101:12, Jun. 6, 1979, pp. 3402–3404.
Chatterjee et al., "On the Structure of Alisamycin, a New Member of the manumycin Class of Antibiotics," The Journal of Antibiotics, vol. 46, No. 6, pp. 1027–1030 (Jun. 1993).
Brodasky et al., "U-56,407, A New Antibiotic Related to Asukamycin: Isolation and Characterization," The Journal of Antibiotics, vol. 36, No. 8, pp. 950–956 (Aug. 1983).

*Primary Examiner*—Joseph E. Evans
*Attorney, Agent, or Firm*—Suzanne E. Babajko

[57] ABSTRACT

Manumycin C, Manumycin D and Manumycin E, obtainable by cultivation of a strain of Streptomyces sp. A.T.C.C. No. 55484, oxidized derivatives thereof and salts and prodrugs of these compounds. The novel compounds have antibacterial and antitumor activity.

12 Claims, 9 Drawing Sheets

MANUMYCIN COMPOUNDS

FIELD OF THE INVENTION

The present invention relates to a novel class of antitumor antibiotic manumycin compounds which may be obtained by cultivation of a strain of Streptomyces sp., to oxidized derivatives thereof, and to salts and prodrugs of these compounds. The present invention also relates to methods of preparing, compositions containing and methods of using the inventive compounds, and to the novel strain of Streptomyces sp.

SUMMARY OF THE INVENTION

Cultivation of a strain of the microorganism Streptomyces sp., which has been deposited in the American Type Culture Collection as A.T.C.C. No. 55484, yields the novel compounds hereinafter referred to as Manumycin C, Manumycin D and Manumycin E. These compounds have been found to have antibiotic activity, particularly in inhibiting the growth of bacteria. In addition, these compounds have been found to inhibit the farnesylation of Ras protein p21, and are therefore expected to be useful as antitumor agents.

The present invention provides the compound Manumycin C having the structure:

corresponding to the name 2,4,6-heptatrienenamide, 7-isopentyl-N-[5-hydroxy-5-[7-[2-hydroxy-5-oxo-1-cyclopenten-1-yl-amino]-7-oxo-1,3,5-heptatrienyl]-2-oxo-7-oxabicyclo[4.1.0]hept-3-en-yl]-, (all-E)-;

Manumycin D having the structure:

corresponding to the name 2,4,6-heptatrienenamide, 7-cyclohexyl-N-[5-hydroxy-5-[7-[2-hydroxy-5-oxo-1-cyclopenten-1-yl-amino]-7-oxo-1,3,5-heptatrienyl]-2-oxo-7-oxabicyclo[4.1.0]hept-3-en-yl]-, (all-E)-; and Manumycin E having the structure:

corresponding to the name 2,4,6-heptatrienenamide, 7-isopropyl-N-[5-hydroxy-5-[7-[2-hydroxy-5-oxo-1-cyclopenten-1-yl-amino]-7-oxo-1,3,5-heptatrienyl]-2-oxo-7-oxabicyclo[4.1.0]hept-3-en-yl]-, (all-E)-.

The present invention also provides oxidized derivatives of the compounds Manumycin C, D and E. The oxidized derivatives, referred to herein as "oxidized Manumycin C", "oxidized Manumycin D", and "oxidized Manumycin E", have, respectively, the following structures:

corresponding to the name 2,4,6-heptatrieneamide 7-isopentyl-N-[2,5-dioxo-7-oxabicyclo (4.1.0)hept-3-en-yl]-(all-E)-;

corresponding to the name 2,4, 6-heptatrieneamide 7-cyclohexyl-N-[2,5-dioxo-7-oxabicyclo(4.1.0)hept-3-en-yl]-(all-E)-; and corresponding to the name 2,4,6-heptatrieneamide 7-isopropyl-N-[2,5-dioxo-7-oxabicyclo(4.1.0)hept-3-en-yl]-(all-E)-.

The present invention further provides salts and prodrugs of Manumycins C, D and E and the oxidized derivatives thereof. It is understood that all stereoisomers of the compounds of the invention are contemplated herein, whether alone (that is, substantially free of other isomers), in a mixture of certain stereoisomers (for example, as a racemate) or in any other mixture thereof.

The compounds of the present invention possess antibiotic activity against a variety of microorganisms, and may therefore be used, for example, to prevent or treat bacterial infections in animals, particularly humans, as well as serve as disinfectants for suppressing bacterial growth, for example, on surfaces such as those of surgical instruments. Manumycin C, Manumycin D and Manumycin E also inhibit the farnesylation of ras oncogene protein p21. The compounds of the present invention may therefore be expected to block the neoplastic effect of ras oncogenes in tumor cells, and thus to be useful in preventing or treating tumors.

The present invention therefore also provides novel compositions comprising, and methods of using, the inventive compounds as antibiotic or antitumor agents, as well as methods of making the inventive compounds, and the novel strain of Streptomyces sp. described herein.

DETAILED DESCRIPTION OF THE INVENTION

The present invention is described further as follows.

The Microorganism

The microorganism which may be used for the production of Manumycin C, Manumycin D and Manumycin E is a strain of Streptomyces sp., which strain was isolated from a soil sample obtained in Princeton, N.J. A subculture of the microorganism may be obtained from the permanent collection of the American Type Culture Collection, 12301 Parklawn Drive, Rockville, Md. 20852, where it was deposited on Oct. 8, 1993 and received the accession number A.T.C.C. No. 55484. In addition to the specific microorganism described herein, it should be understood that mutants, such as those produced by the use of chemical or physical mutagens including X-rays, etc. and organisms whose genetic makeup has been modified by molecular biology techniques, may also be cultivated to produce Manumycin C, Manumycin D and Manumycin E.

Isolation of the microorganism from a soil sample in which it is present may be accomplished by placing about 0.5 to 1.0 g of soil in a tube with 10 ml of a sterile solution containing 0.01% gelatin and salts. After vigorous shaking, a small aliquot of a dilution of the suspension is placed onto the surface of a nutrient agar medium in a Petri dish. The composition of an exemplary such medium is:

| | |
|---|---|
| Glycerol | 12.5 g |

-continued

| | |
|---|---|
| Arginine | 1.0 g |
| NaCl | 20.0 g |
| K$_2$HPO$_4$ | 1.0 g |
| MgSO$_4$.7H$_2$O | 0.5 g |
| Fe(SO$_4$)$_3$.6H$_2$O | 0.01 g |
| CuSO$_4$.5H$_2$O | 0.001 g |
| ZnSO$_4$.7H$_2$O | 0.001 g |
| MnSO$_4$.H$_2$O | 0.008 g |
| Agar | 15.0 g |
| Distilled water | 1.0 liter |
| Cycloheximide* | 10.0 ml of 1% aqueous solution |

*Filter sterilized and added aseptically to the remainder of the medium, which has been adjusted to a pH of about 7 and sterilized by autoclaving at 121° C. for 30 minutes prior to the addition of the cycloheximide.

After 5 to 8 days incubation at room temperature, the colonies of Streptomyces sp. A.T.C.C. No. 55484 may be isolated from the plated soil sample and transferred to slants of a nutrient agar of the following composition:

| | |
|---|---|
| Soil extract* solution | 200.0 ml |
| Yeast extract | 5.0 g |
| Glucose | 5.0 g |
| Tap water | 800.0 ml |
| Agar | 17.5 g |

*The soil extract solution is made by boiling a suspension of soil in water (1:2, soil:water v/v) for 1 hour and filtering the cooled extract.

The culture may subsequently be maintained at −80° C. as a suspension of vegetative cells. This suspension may be prepared as described in Example 1.

Two-week old mature cultures show gray (ISCC-NBS #93) aerial mycelium and development of smooth spores borne in Spiral (S) spore chains when grown on any of the ISP morphology media: Yeast Malt Agar (ISP medium 2), Oatmeal Agar (ISP medium 3), Inorganic Salts-Starch Agar (ISP medium 4). Substrate mycelium on Asparagine Agar (ISP medium 5) is yellowish/tan (Prauser color code Coo2r).

The reverse shows a dark yellow brown pigment on all morphology media with no diffusible pigment on Tyrosine Agar (ISP medium 7), Yeast Malt Agar (ISP medium 2) and Oatmeal Agar (ISP medium 3). No melanoid pigments were noted on Peptone-Iron Agar (ISP medium 6) or on Tyrosine Agar (ISP medium 7). This was confirmed by the modified Arai and Mikami melanin formation test (*International Journal of Systematic Bacteriology*, 27:3, p. 290 (1977)).

The following carbon sources were utilized for growth: Glucose, Xylose, Rhamnose, Fructose (weak), Raffinose, Galactose and Salicin (weak). No growth was observed on Mannitol, Inositol, Sorbitol, Arabinose or Sucrose. Growth patterns were read at 7, 14 and 21 days of incubation at 28° C. on ISP medium 9 as a basal medium supplemented with the appropriate carbon sources according to the International Streptomyces Project Methods (*International Journal of Systematic Bacteriology*, 16:313–340).

The characteristics of this culture are consistent with those of Streptomyces sp. in all respects except for the utilization of mannitol.

The present invention provides the above novel strain of Streptomyces sp. designated by A.T.C.C. No. 55484, which may be isolated from soil such as by the cultivation and isolation methods described herein. Also provided are organisms which have the identifying characteristics of the strain designated by A.T.C.C. No. 55484 as discussed above, and which are capable of producing Manumycins C, D or E. Such organisms include those originally designated as Streptomyces sp. A.T.C.C. No. 55484 which have been modified by physical, chemical, or biological means. Substantially pure, especially biologically pure, cultures of the organisms described herein are preferred.

The Novel Compounds

The novel antibiotics Manumycin C, Manumycin D and Manumycin E may be produced by fermentation of Streptomyces sp. A.T.C.C. No. 55484, or by a microorganism having the identifying characteristics of the aforementioned Streptomyces sp. and which is capable of producing said compounds, and isolating one or more of said compounds from the fermentation broth. For example, Manumycin C, Manumycin D and Manumycin E may be produced by cultivation of Streptomyces sp. A.T.C.C. No. 55484 at or about a temperature of 18° C. to 32° C., preferably at 28° C., under submerged aerobic conditions in an aqueous medium containing assimilable sources of carbon and nitrogen and other optional nutrients. The fermentation is preferably carried out until substantial antibiotic activity is imparted to the medium, usually about 120 to 144 hours. The fermentation, as well as subsequent isolation steps, may be monitored by means of thin layer chromatography and bioautography against a hyperpermeable strain of *Escherichia coli* (e.g., *E. coli* impB) and by agar diffusion assay against a hyperpermeable *Escherichia coli* strain.

Manumycin C, Manumycin D and Manumycin E may be isolated and purified by means of art-recognized techniques from the fermentation broth. To obtain these antibiotics from the fermentation broth, the antibiotics may be extracted into ethyl acetate which is then concentrated in vacuo to a residue. The residue is dissolved in aqueous methanol and the resulting solution is extracted first with hexane and then with carbon tetrachloride to remove impurities. Further purification is effected by extraction of the active agents from the aqueous methanol layer into chloroform and subsequent flash chromatography of the chloroform-soluble fraction on silica gel. Separation of the three active principles and final purification is then accomplished by reversed phase HPLC, to yield pure Manumycin C, Manumycin D and Manumycin E as yellow amorphous powders.

The term "salts", as used herein, denotes acidic and/or basic salts, formed with inorganic or organic acids and/or bases, preferably basic salts. While pharmaceutically acceptable salts are preferred, particularly when employing the compounds of the invention as medicaments, other salts find utility, for example, in processing these compounds, or where non-medicament-type uses are contemplated. Salts of these compounds may be prepared by art-recognized techniques. For example, Manumycins C, D or E may be converted into their respective alkali metal or amine salts by treatment with alkali metal hydroxide or amine, respectively. Preferably, Manumycins C, D and E are converted to their respective sodium or triethylamine salts by treatment with sodium hydroxide or triethylamine (especially, one molar equivalent of sodium hydroxide or triethylamine) in water, followed by lyophilization, to yield water soluble salts of Manumycins C, D and E in which the hydroxyl (HO) moiety on the cyclopentenyl group is converted to the moiety $Na^+O^-$ (when sodium hydroxide is employed) or $Et_3N^+O^-$ (when triethylamine is employed ($Et=ethyl$)).

The term "prodrug", as used herein, denotes compounds which, in vivo, undergo chemical conversion to Manumycin C, Manumycin D or Manumycin E, their oxidized derivatives, or salts thereof. Prodrug compounds may be prepared by art-recognized techniques such as those described in *Design of Prodrugs*, edited by H. Bundgaard (Elsevier, 1985). Water soluble prodrugs are preferred, for example, prodrugs of Manumycins C, D, or E in which the hydroxyl (HO) moiety on the cyclopentenyl group is converted to the moiety $H_3CO-C(O)-CH_2-SO_2-CH_2-C(O)-O-$ (Nicolaou et al., *Nature*, 364, pp. 464–466 (1993)).

The oxidized derivatives of Manumycins C, D and E described herein may be prepared by contacting Manumycin C, D or E with chromic acid (see *J. Antibiotics*, Vol. XL, pp. 1530–1540 (1987)) to effect oxidation and form the ketone moiety. The oxidized derivatives may have the same or increased biological activity vis-a-vis the parent Manumycin C, D or E compound.

Utility

The novel compounds of the present invention include Manumycins C, D and E, oxidized Manumycins C, D and E, and salts and prodrugs thereof (it being understood that stereoisomers of these compounds are included as described above).

It is preferred that the inventive compounds have a degree of purity such that they are suitable for use as an antibiotic and/or antitumor agent. A particularly preferred embodiment of the present invention provides Manumycin C, Manumycin D, or Manumycin E or an oxidized derivative, or a salt or prodrug thereof, in its pure or substantially pure state. The pure or substantially pure compounds are preferably employed in preparing compositions such as those of the present invention. Further, the pure or substantially pure compounds, alone or as used in compositions exemplified by those described herein, are preferably employed in the methods of the present invention. It is understood that a single, or two or more, compound(s) of the present invention may be employed in any of the compositions or methods described herein.

The inventive compounds are useful as antimicrobial agents, having utility in inhibiting the growth of, including killing, microorganisms. The inventive compounds are particularly useful as broad spectrum antibacterial agents, having activity against both gram-positive and gram-negative bacteria. Thus, the compounds of the present invention may be employed in utilities suitable for such antimicrobial agents.

The inventive compounds may, for example, be used in treating a host infected with a bacterium, or in preventing infection of said host by said bacterium, comprising the step of administering to the host Manumycin C, Manumycin D, Manumycin E, an oxidized derivative, or a physiologically tolerated salt or prodrug thereof in an amount effective for said prevention or treatment. Treatment of such infections according to the present invention includes both mitigation as well as elimination thereof.

Hosts administered the inventive compounds may be plants or animals, particularly animals such as dogs, cats and other domestic mammals and, especially humans. The dosage form and mode of administration, as well as the dosage amount, may be selected by one of ordinary skill in the art. The dosage amount will vary with the severity of the infection, and with the size and species of the host. Exemplary daily dosages for an adult human are those within the range of from about 2.5 mg to about 200 mg/day. Administration to a mammalian host may, for example, be oral, topical, rectal or parenteral. Administration to a plant host may be accomplished by, for example, application to seed, foliage or other plant part, or to the soil.

Compositions are also provided by the present invention which comprise Manumycin C, Manumycin D or Manumycin E, an oxidized derivative, or a physiologically tolerated salt or prodrug thereof in an amount effective for the prevention or treatment of infection by a bacterium, and a physiologically tolerated vehicle or diluent. The term "physiologically tolerated" is equivalent to the term "pharmaceutically acceptable" when used in reference to the treatment of a mammalian host. The appropriate solid or liquid vehicle or diluent may be selected, and the compositions prepared, by methods known to one of ordinary skill in the art. Prevention or treatment of simultaneous infections by more than one bacterium is, of course, contemplated.

The inventive compounds may also be employed as antimicrobial agents useful in inhibiting the growth of, including killing, microorganisms present on a surface or in a medium outside a living host. The present invention therefore provides a method for inhibiting the growth of at least one bacterium present on a surface or in a medium, comprising the step of contacting the surface or medium with Manumycin C, Manumycin D or Manumycin E, an oxidized derivative, or a salt or prodrug thereof in an amount effective for the inhibition. Thus, the inventive compounds may be employed, for example, as disinfectants for surface treatments, such as disinfection of surgical instruments, or as preservatives for a variety of solid and liquid media susceptible to microbial growth. Suitable amounts of the inventive compounds may be determined by methods known to one of ordinary skill in the art. Compositions comprising Manumycin C, Manumycin D or Manumycin E, an oxidized derivative, or a salt or prodrug thereof in an amount effective for inhibiting the growth of at least one bacterium, and a vehicle or diluent, are also provided by the present invention.

Manumycin C, Manumycin D and Manumycin E have been found to inhibit the farnesylation of ras oncogene protein p21, and thus may be expected to block the neoplastic effect of ras oncogenes in tumor cells. Thus, the present invention provides a method for preventing or treating a tumor in a host, comprising the step of administering to the host Manumycin C, Manumycin D or Manumycin E, an oxidized derivative, or a physiologically tolerated salt or prodrug thereof in an amount effective for such prevention or treatment. Treatment according to the method of the present invention includes maintaining or reducing the size, as well as the elimination of, the tumor. The inventive compounds may be used to treat tumors susceptible to such treatment, including colon, lung and pancreatic tumors. Antitumor compositions containing the inventive compounds are provided, comprising Manumycin C, Manumycin D or Manumycin E, an oxidized derivative, or a physiologically tolerated salt or prodrug thereof in an amount effective for the prevention or treatment of a tumor, and a physiologically tolerated vehicle or diluent.

Hosts, dosages, modes of administration, etc., described above for the treatment of a host infected with a bacterium, apply to the use of the present compounds as antitumor agents, and those descriptions are incorporated herein.

The following examples further illustrate the invention, and are not intended to in any way limit the present claims.

EXAMPLE 1

Preparation of Manumycin C, Manumycin D and Manumycin E

A culture of Streptomyces sp. A.T.C.C. No. 55484 was prepared by growing this microorganism on agar slants of ISP-4 medium, and after 7 to 10 days incubation at 28° C. transferring the surface growth to 100 ml of a broth medium of the following composition in a cotton-stoppered, sterile 500 mL Erlenmeyer flask:

| | |
|---|---|
| Soluble starch | 5.0 g |
| Glucose | 5.0 g |
| Fishmeal extract | 1.0 g |
| Yeast extract | 2.0 g |
| NZ case | 2.0 g |
| NaCl | 2.0 g |
| $CaCO_3$ | 1.0 g |
| Deionized water | q.s. to 1 liter |

The flasks were incubated at 28° C. for 72 hours on a rotary shaker operating at 250 rpm. At harvest, four ml portions of the culture were withdrawn and diluted with equal volumes of a cryoprotective solution consisting of:

| | |
|---|---|
| Sucrose | 100 g |
| Glycerol | 200 g |
| Deionized water | q.s. to 1000 ml |

The suspensions were then frozen in a dry-ice acetone bath and stored at −80° C. The cultures were maintained at −80° C. as frozen vegetative cultures.

When needed to prepare inoculum, 4 mL of frozen vegetative culture was transferred to each of two Erlenmeyer flasks containing 100 mL of medium per 500 mL flask. The medium had the same composition as did the broth medium used to prepare the cryopreserved culture. The flasks were incubated under the same conditions as described above. After incubation for 72 hours, 4 mL of the growth was used to inoculate 50 Erlenmeyer flasks, each containing 100 mL of medium per 500 ml flask. The composition of this medium was:

| | |
|---|---|
| Pharmamedia | 20 g |
| Glucose | 50 g |
| $CaCO_3$ | 7 g |
| Deionized water | to 1000 ml |

The medium was sterilized at 121° C. for 20 minutes prior to use.

The inoculated flasks were incubated at 28° C. on a rotary shaker operating at 250 rpm for 120 to 144 hours and harvested. At that time, the contents of the flasks were collected and pooled. Ethyl acetate (5 L) was added to the pool and the whole stirred vigorously for 1 hour. The ethyl acetate layer was separated and concentrated in vacuo to yield 7.1 g of a brown oil. The oil was dissolved in a mixture of methanol (100 mL) and water (11 mL) and the solution extracted with hexane (111 ml×2) to remove impurities. The hexane layers were discarded. Water (22 ml) was added to the remaining methanol-water layer and the resulting solution was extracted with carbon tetrachloride (133 mL×2). The carbon tetrachloride layers were removed and discarded. Water (21 mL) was again added to the remaining methanol-water layer and the resulting solution was extracted with chloroform (154 mL×2). The chloroform layers were separated, pooled and concentrated in vacuo to a brown oil (0.64 g). The oil was purified further by flash chromatography on a silica gel 60 column (EM Science, 120 g), developing first with methylene chloride (2 L), then with 2 L of chloroform-methanol (100:2), and finally with 2 L of a solvent mixture consisting of chloroform-methanol-water (100:3:0.5). Fifty ml fractions were collected. The active fractions were pooled and concentrated in vacuo to yield a yellow amorphous powder, 0.19 g. The powder was washed three times with a mixture of toluene:-methylene chloride (3:1), leaving a yellow precipitate (0.12 g). A portion of the precipitate (63 mg) was dissolved in dimethylsulfoxide and charged onto a reversed phase HPLC column (Dynamax C18, 60 Å pore size) and eluted with a gradient begining with 40% 0.01M potassium dihydrogen phosphate and 60% acetonitrile/methanol (3:1, v/v) and ending with a solvent of 100% acetonitrile/methanol (3:1, v/v) over a time course of 50 minutes. The flow rate was 4 ml per minute; detection was by UV absorption at 250 nm. The three novel compounds of this invention eluted as follows: Manumycin C at 17.2 minutes, Manumycin D at 24.8 minutes and Manumycin E at 26.8 minutes. The appropriate eluates were combined to give 9.0 mg of pure Manumycin C, 6.5 mg of pure Manumycin D and 7.5 mg of pure Manumycin E.

Figure 1:
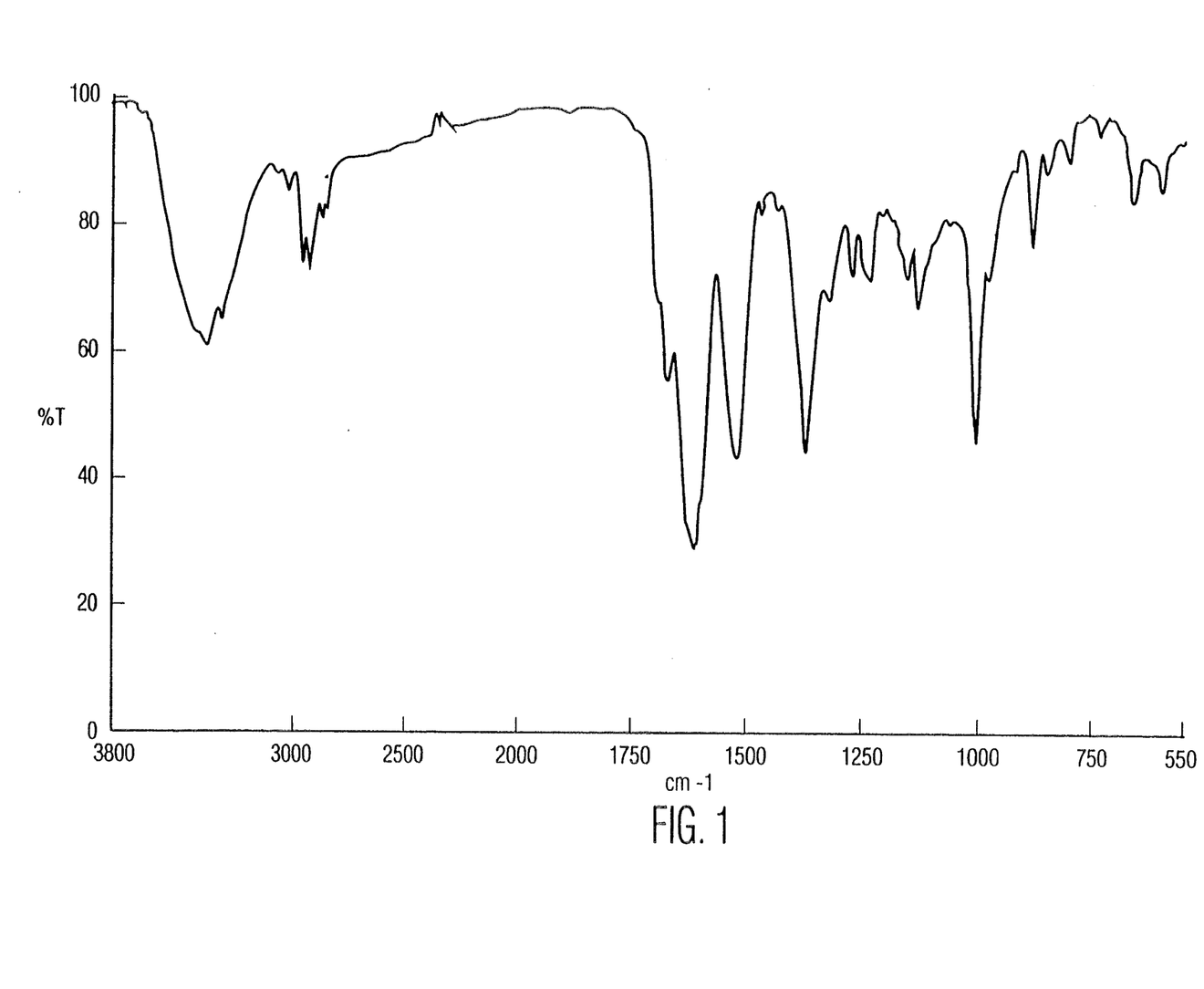
FIG. 1 shows the IR spectrum of Manumycin C (KBr pellet).
Figure 2:
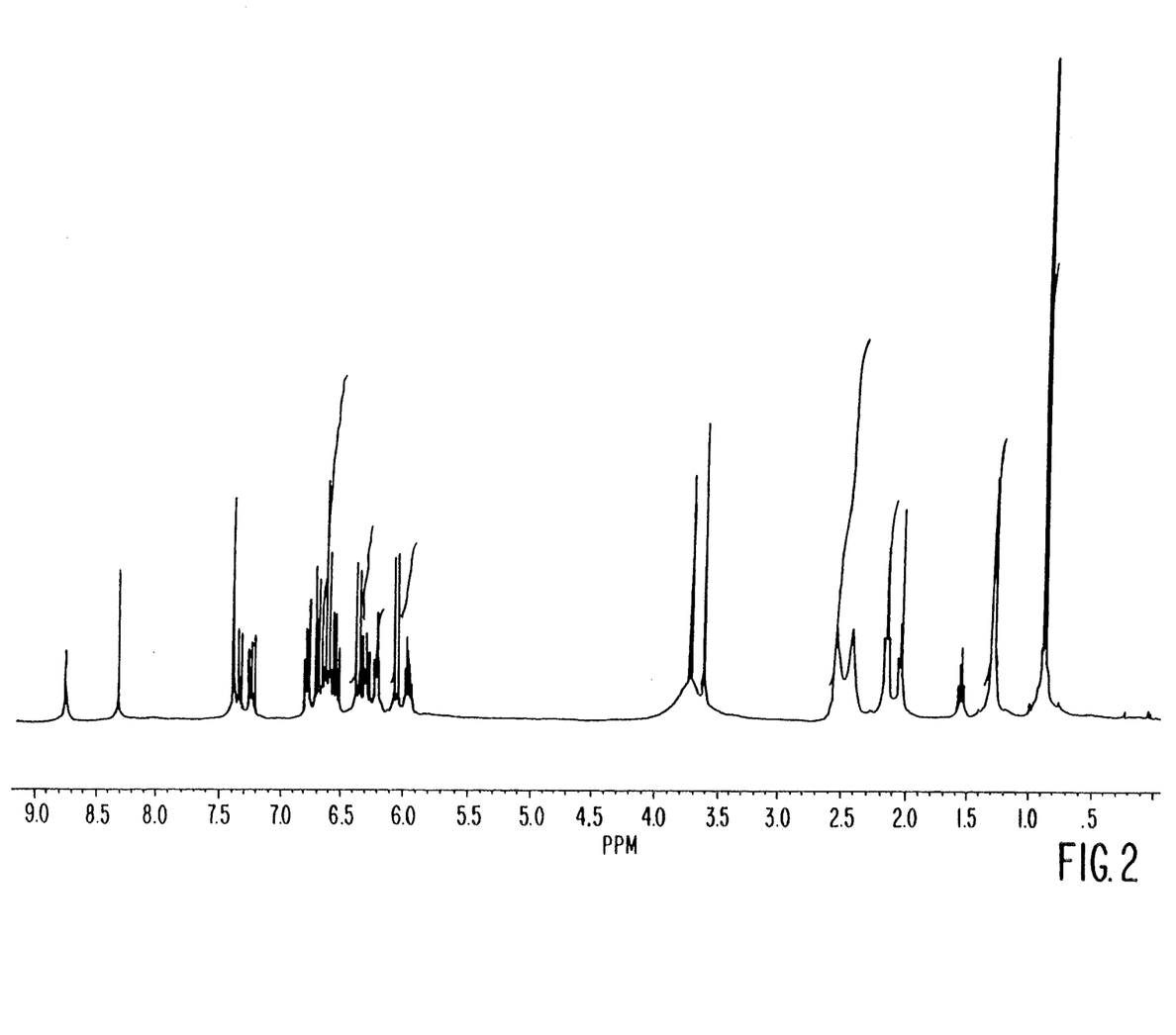
FIG. 2 shows the $^1$H NMR spectrum of Manumycin C in acetone-$d_6$.
Figure 3:
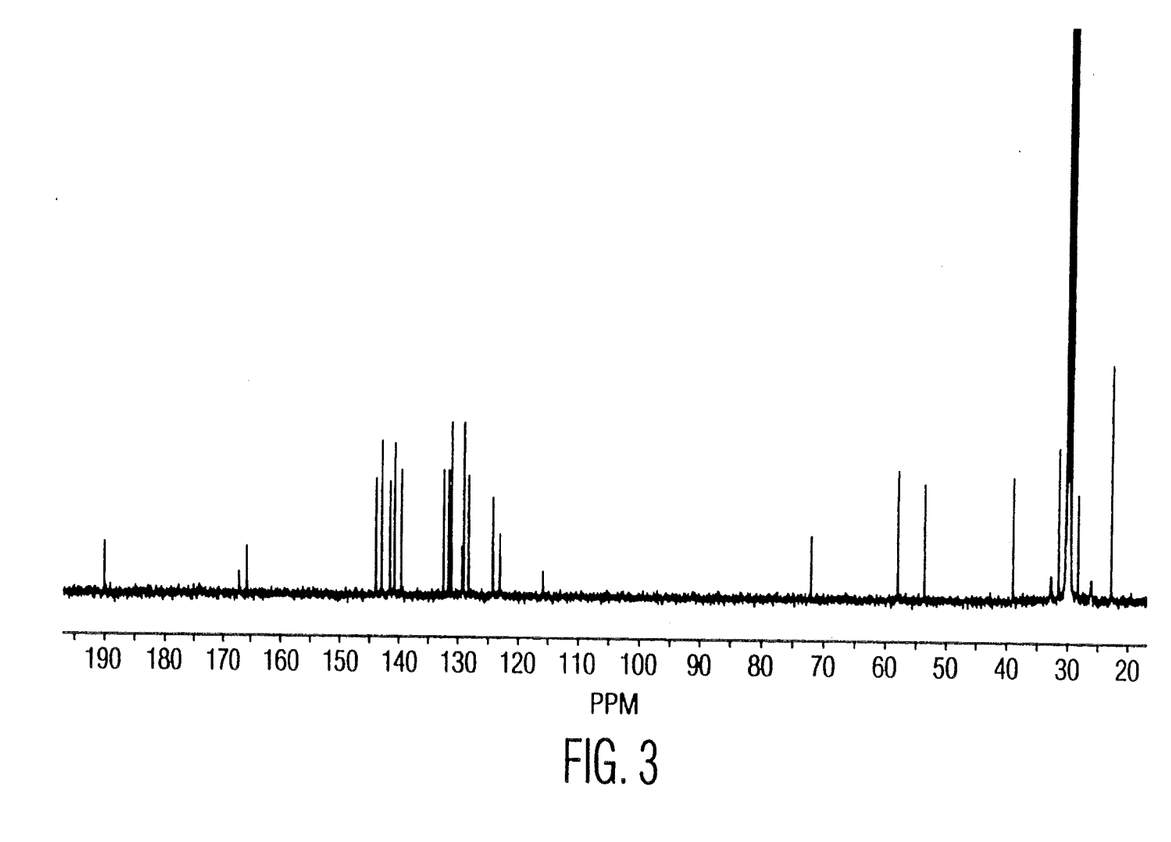
FIG. 3 shows the $^{13}$C NMR spectrum of Manumycin C in acetone-$d_6$.

Manumycin C, a yellow amorphous powder soluble in dimethyl sulfoxide, acetone, and acetonitrile and insoluble in water and hexane has been found to have the following characteristics: high resolution mass spectrum m/z 534.2347 (calc. for $C_{30}H_{34}N_2O_7$ is 534.2366); UV spectrum in acetonitrile, absorption maximum (log $\epsilon$) at 316 nm (4.39); infrared spectrum in KBr, major absorption maxima ($cm^{-1}$) 3400, 3320, 2930, 1700, 1640, 1545, 1380 and 1000 (FIG. 1); $(\alpha)_D$ value of $+128°$ (c=0.01, $CH_3COCH_3$); $^1H$ NMR spectrum (500 MHz) in acetone-$d_6$, Table 1 and FIG. 2; $^{13}C$ NMR spectrum (125 MHz) in acetone-$d_6$, in Table 2 and FIG. 3.

Figure 4:
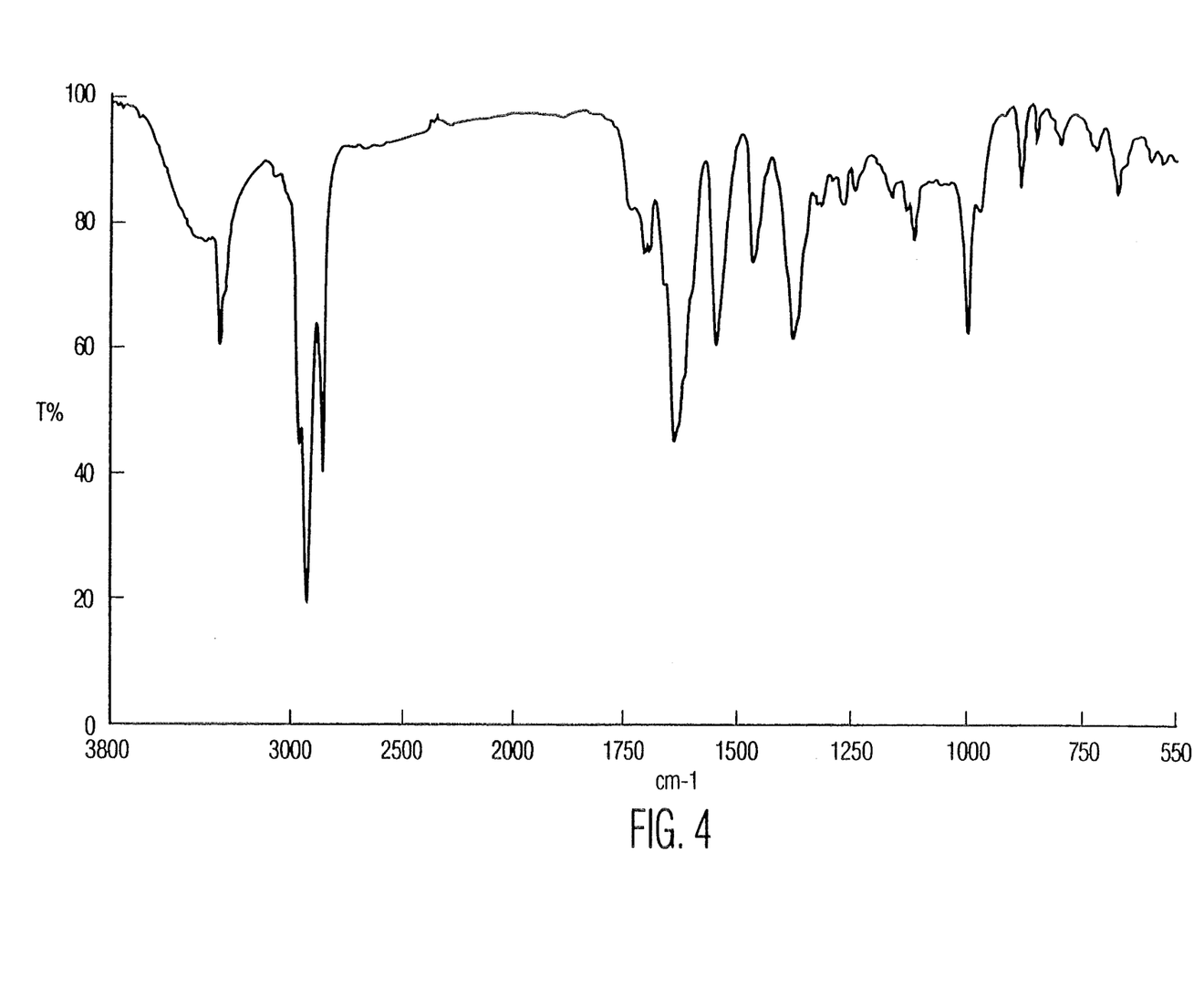
FIG. 4 shows the IR spectrum of Manumycin D (KBr pellet).
Figure 5:
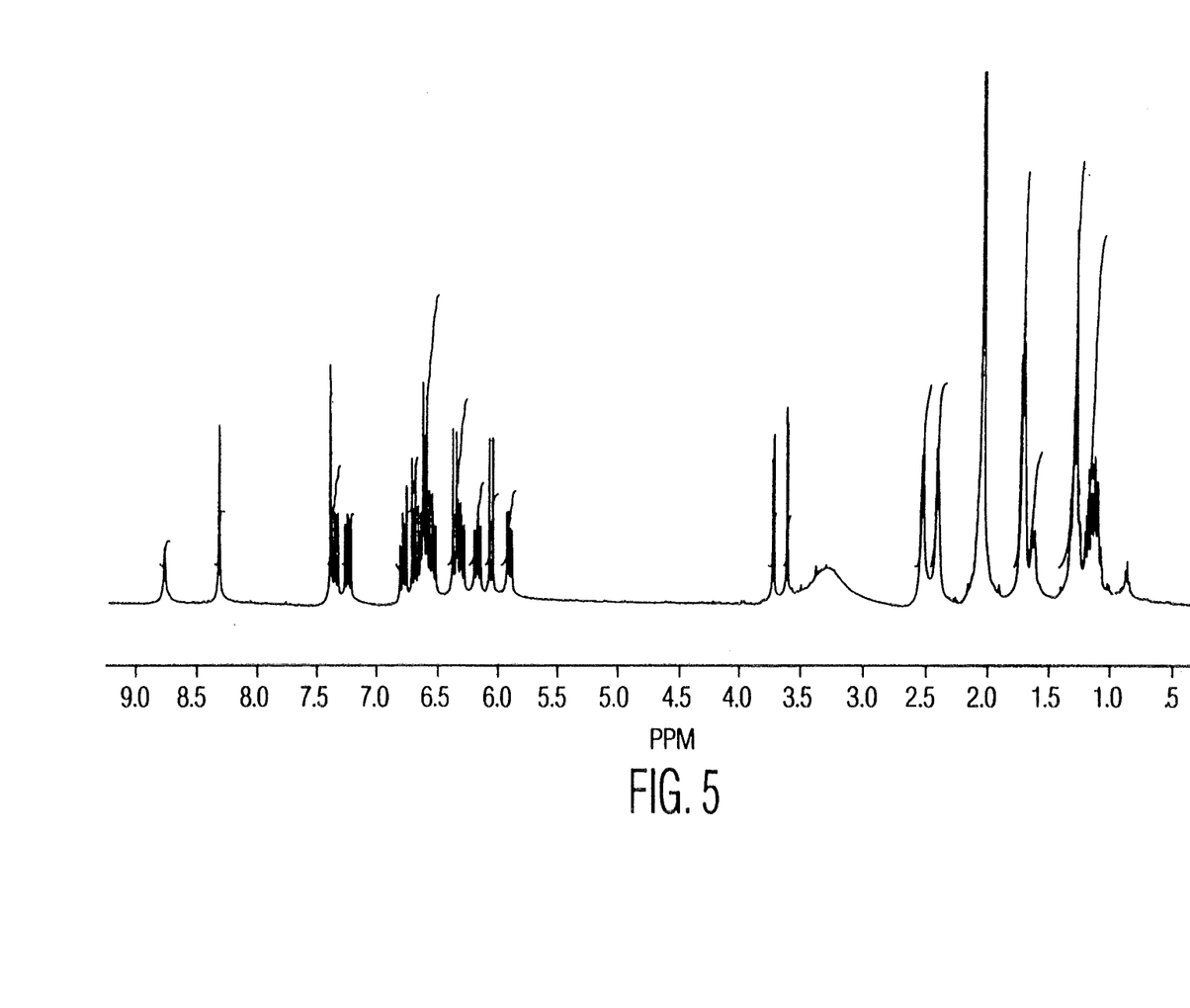
FIG. 5 shows the $^1$H NMR spectrum of Manumycin D in acetone-$d_6$.
Figure 6:
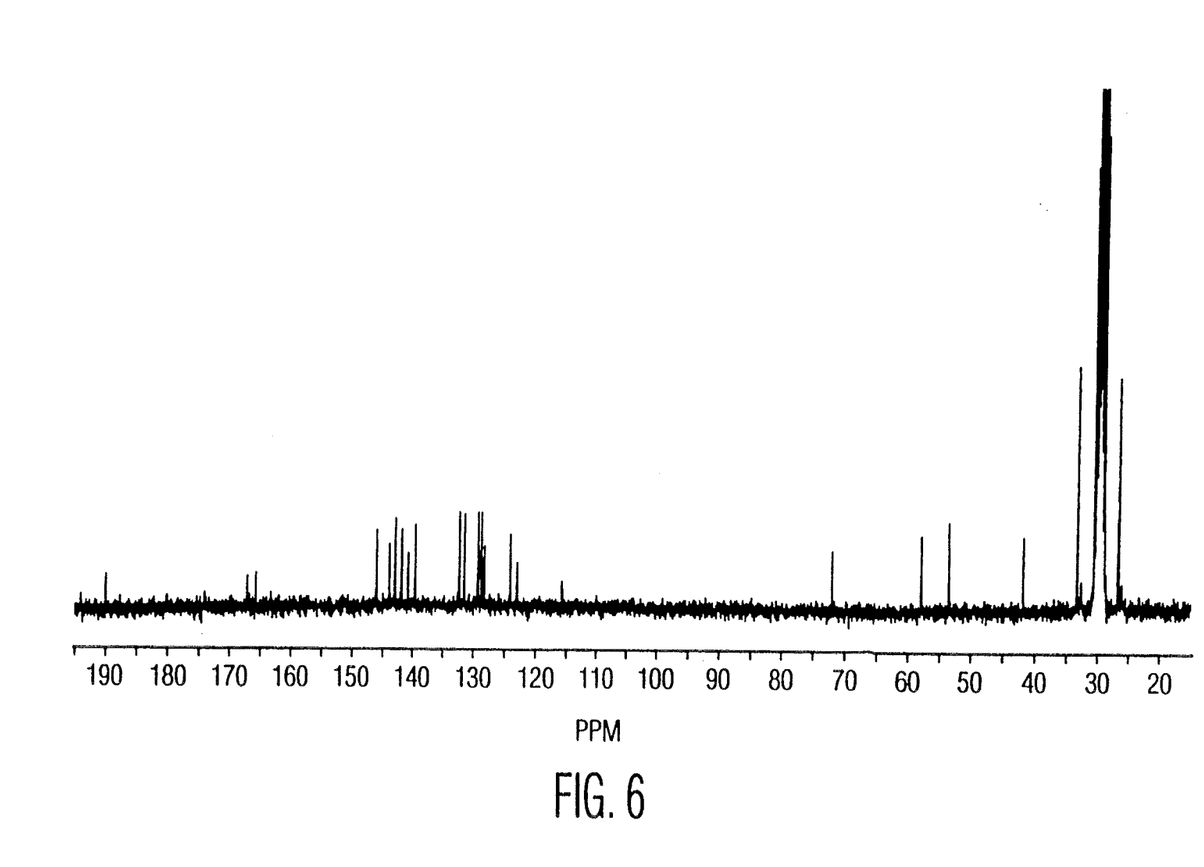
FIG. 6 shows the $^{13}$C NMR spectrum of Manumycin D in acetone-$d_6$.

Manumycin D, a yellow amorphous powder soluble in dimethyl sulfoxide, acetone, and acetonitrile and insoluble in water and hexane has been found to have the following characteristics: high resolution mass spectrum m/z 546.2360 (calc. for $C_{31}H_{34}N_2O_7$ is 546.2366); UV spectrum in acetonitrile, absorption maximum (log $\epsilon$) at 316 nm (4.48); infrared spectrum in KBr, major absorption maxima ($cm^{-1}$) of the major bands were: 3400, 2930, 1675, 1620, 1520, 1370 and 1000 (FIG. 4); $(\alpha)_D$ value of $+500°$ (c=0.03, $CH_3CN$); $^1H$ NMR spectrum (500 MHz) in acetone-$d_6$, in Table 1 and FIG. 5; $^{13}C$ NMR spectrum (125 MHz) in acetone-$d_6$, in Table 2 and FIG. 6.

Figure 7:
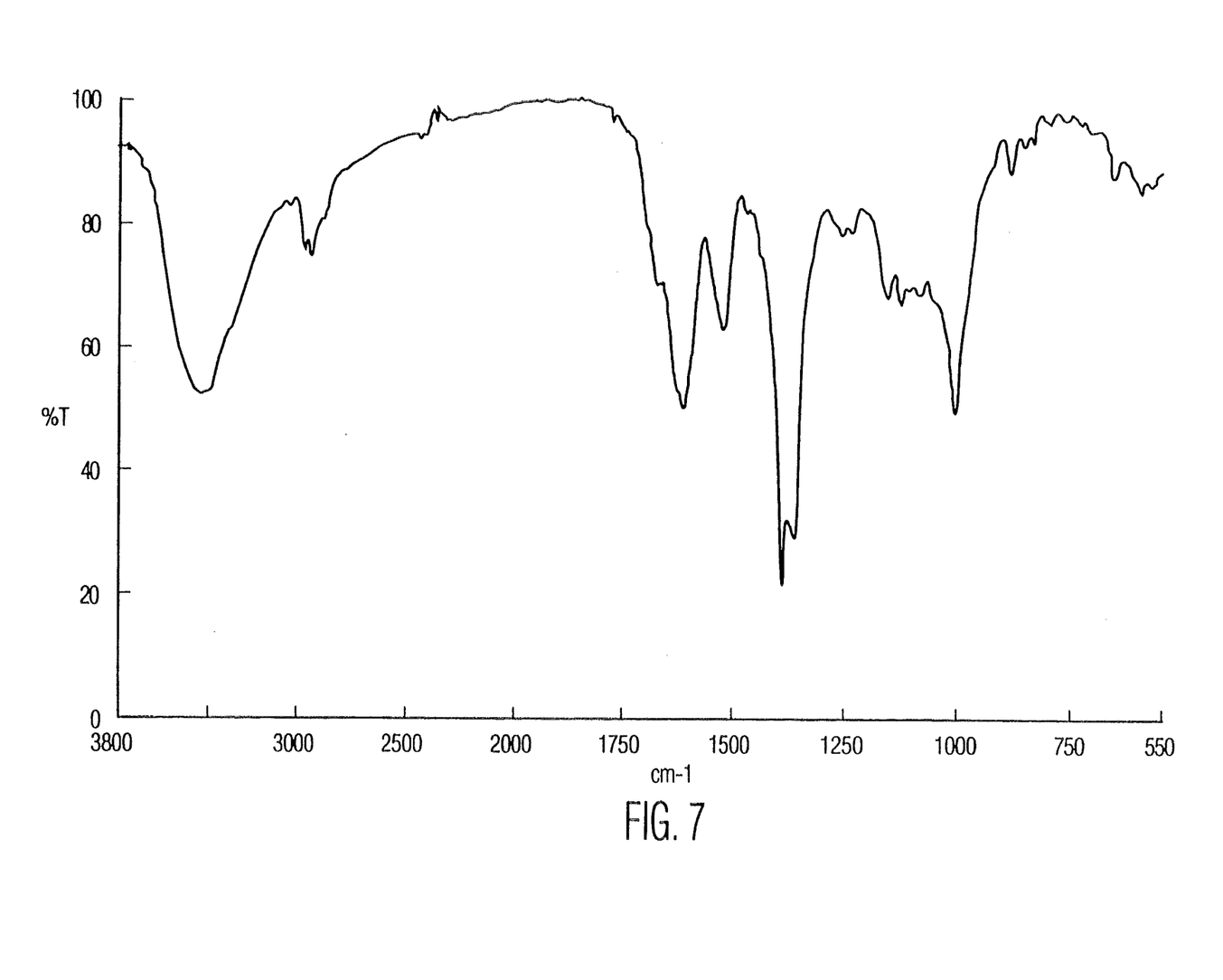
FIG. 7 shows the IR spectrum of Manumycin E (KBr pellet).
Figure 8:
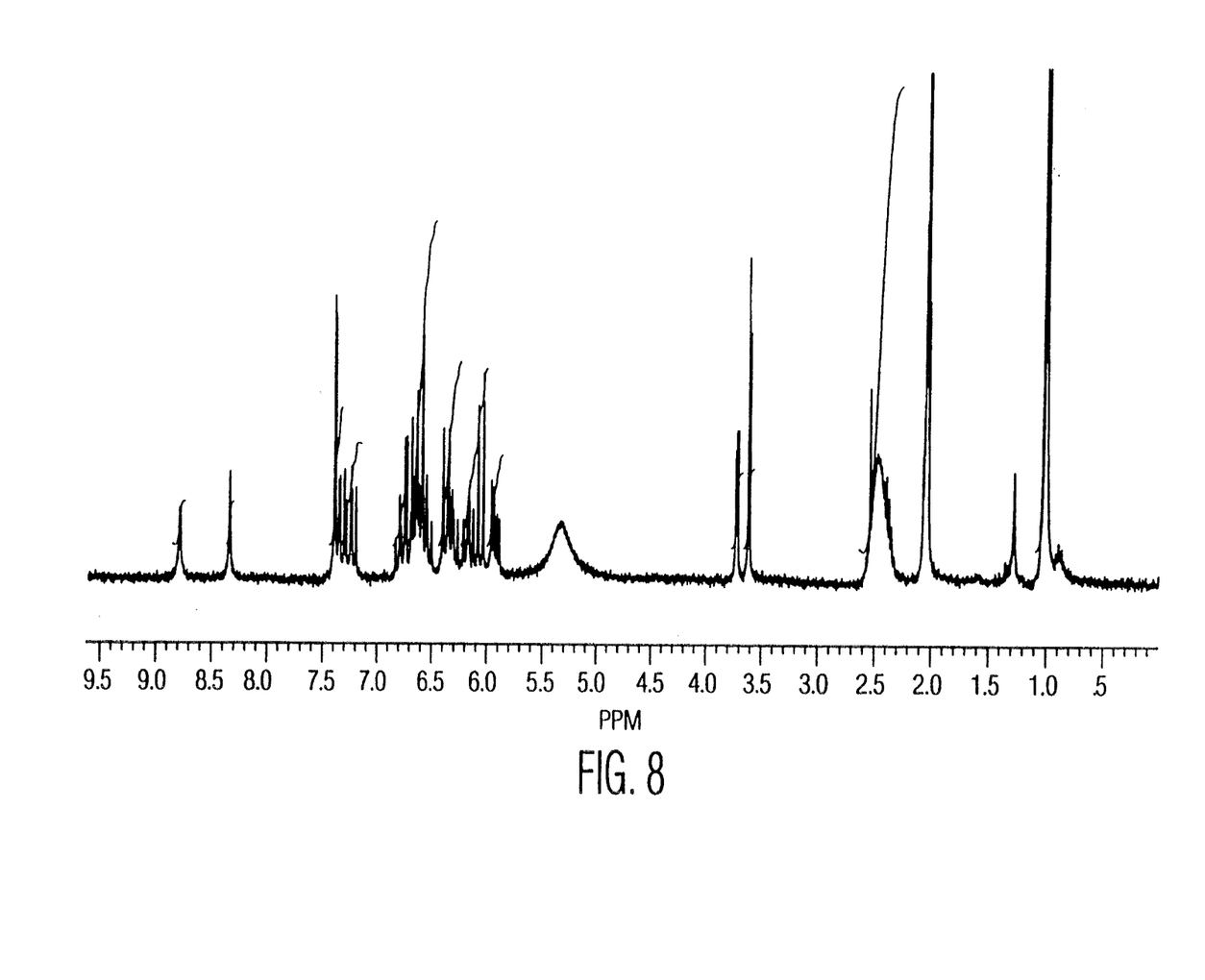
FIG. 8 shows the $^1$H NMR spectrum of Manumycin E in acetone-$d_6$.
Figure 9:
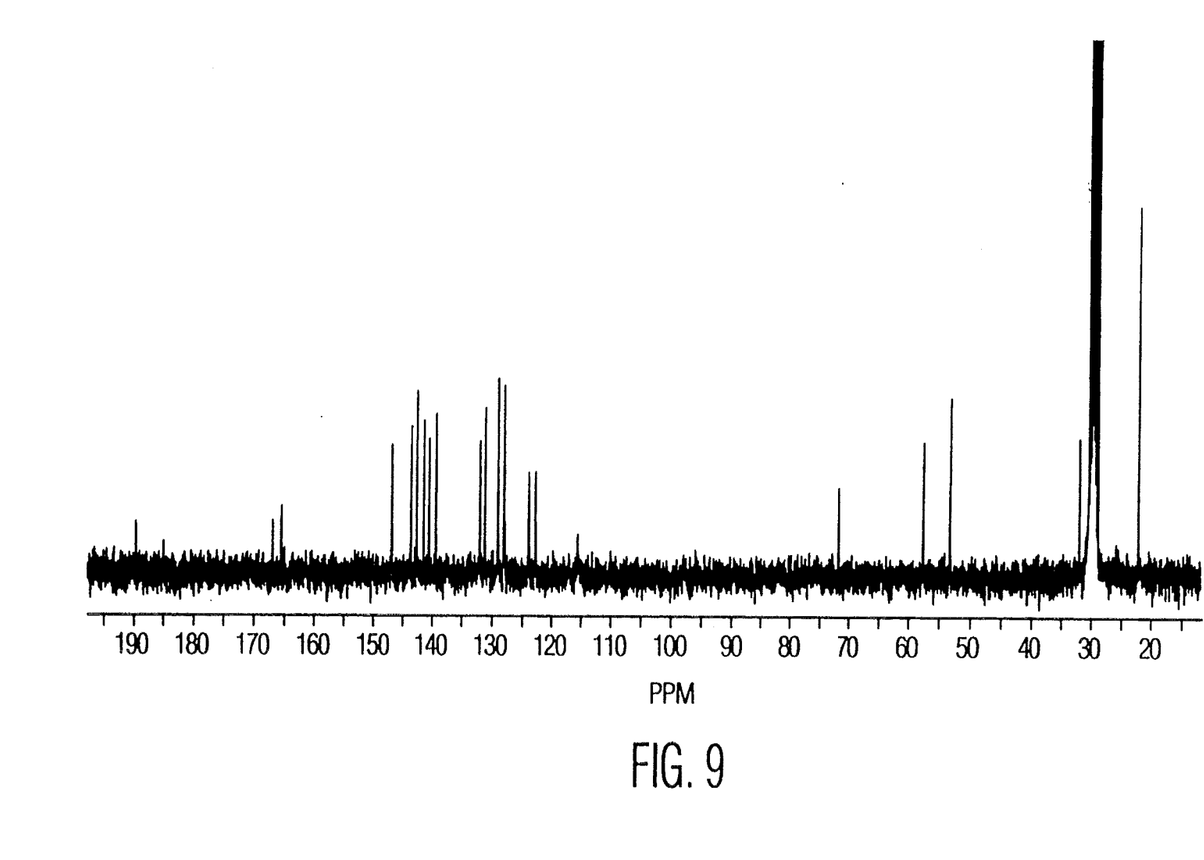
FIG. 9 shows the $^{13}$C NMR spectrum of Manumycin E in acetone-$d_6$.

Manumycin E, a yellow amorphous powder soluble in dimethyl sulfoxide, acetone, and acetonitrile and insoluble in water and hexane has been found to have the following characteristics: high resolution mass spectrum m/z 506.2039 (calc. for $C_{28}H_{30}N_2O_7$ is 506.2053); UV spectrum in acetonitrile, absorption maximum (log $\epsilon$) at 312 nm (4.50); infrared spectrum in KBr, major absorption maxima ($cm^{-1}$) of the major bands were: 3425, 2930, 1670, 1610, 1520, 1380, 1310 and 1000 (FIG. 7); $(\alpha)_D$ value of $+380°$ (c=0.02, $CH_3CN$); $^1H$ NMR spectrum (500 MHz) in acetone-$d_6$, in Table 1 and FIG. 8; $^{13}C$ NMR spectrum (125 MHz) in acetone-$d_6$, in Table 2 and FIG. 9.

| Proton Position | Manumycin C $\delta ^1H$ ppm (mult. Hz) |
|---|---|
| H-3 | 7.38 (d, 2.8) |
| H-5 | 3.72 (dd, 2.8, 4.2) |
| H-6 | 3.61 (d, 4.2) |
| H-7 | 6.07 (d, 14.9) |
| H-8 | 6.68 (dd, 14.9, 11.0) |
| H-9 | 6.78 (dd, 14.5, 11.0) |
| H-10 | 6.55 (dd, 14.5, 11.4) |
| H-11 | 7.36 (dd, 14.8, 11.4) |
| H-12 | 6.60 (d, 14.8) |
| H-2' | 6.36 (d, 14.9) |
| H-3' | 7.24 (dd, 14.8, 11.4) |
| H-4' | 6.31 (dd, 14.9, 11.4) |
| H-5' | 6.62 (dd, 14.9, 10.7) |
| H-6' | 6.21 (dd, 15.1, 10.7) |
| H-7' | 5.92 (dt, 15.1, 7.1) |
| H-8' | 2.15 (dd, 14.6, 7.1) |
| H-9' | 1.30 (m) |
| H-10' | 1.56 (sep, 6.7) |
| H-11' | 0.88 (d, 6.7) |
| H-12' | 0.88 (d, 6.7) |
| H-13' | |
| H-4'' | 2.53 (br s) |
| H-5'' | 2.42 (br s) |
| NH-14 | 8.77 (s) |
| NH-0' | 8.32 (s) |

| Proton Position | Manumycin D $\delta ^1H$ ppm (mult. Hz) |
|---|---|
| H-3 | 7.38 (d, 2.8) |
| H-5 | 3.72 (dd, 2.8, 4.1) |
| H-6 | 3.61 (d, 4.1) |
| H-7 | 6.07 (d, 15.0) |
| H-8 | 6.70 (dd, 15.0, 11.0) |
| H-9 | 6.78 (dd, 14.5, 11.0) |
| H-10 | 6.55 (dd, 14.5, 11.4) |
| H-11 | 7.36 (dd, 14.8, 11.4) |
| H-12 | 6.63 (d, 14.8) |
| H-2' | 6.36 (d, 14.9) |
| H-3' | 7.24 (dd, 14.8, 11.4) |
| H-4' | 6.31 (dd, 14.9, 11.4) |
| H-5' | 6.62 (dd, 14.9, 10.7) |
| H-6' | 6.17 (dd, 15.3, 10.7) |
| H-7' | 5.92 (dd, 15.3, 7.0) |
| H-8' | 2.07 (m) |
| H-9' | 1.73 (m), 1.12 (m) |
| H-10' | 1.72 (m), 1.31 (m) |
| H-11' | 1.60 (m), 1.12 (m) |
| H-12' | 1.72 (m), 1.31 (m) |
| H-13' | 1.73 (m), 1.12 (m) |
| H-4'' | 2.53 (br s) |
| H-5'' | 2.41 (br s) |
| NH-14 | 8.76 (s) |
| NH-0' | 8.31 (s) |

| Proton Position | Manumycin E $\delta ^1H$ ppm (mult. Hz) |
|---|---|
| H-3 | 7.38 (d, 2.6) |
| H-5 | 3.72 (dd, 2.6, 4.1) |
| H-6 | 3.60 (d, 4.2) |
| H-7 | 6.06 (d, 14.8) |
| H-8 | 6.70 (dd, 14.8, 11.0) |
| H-9 | 6.79 (dd, 14.3, 11.0) |
| H-10 | 6.53 (dd, 14.3, 11.6) |
| H-11 | 7.36 (dd, 15.1, 11.6) |
| H-12 | 6.62 (d, 15.1) |
| H-2' | 6.37 (d, 14.8) |
| H-3' | 7.24 (dd, 14.8, 11.4) |
| H-4' | 6.32 (dd, 14.8, 11.4) |
| H-5' | 6.66 (dd, 14.9, 10.7) |
| H-6' | 6.17 (dd, 15.2, 10.7) |
| H-7' | 5.92 (dd, 15.2, 6.8) |
| H-8' | 2.39 (sep, 6.8) |

-continued

| | |
|---|---|
| H-9' | 1.00 (d, 6.7) |
| H-10' | 1.00 (d, 6.7) |
| H-11' | |
| H-12' | |
| H-13' | |
| H-4" | 2.44 (br s) |
| H-5" | 2.44 (br s) |
| NH-14 | 8.78 (s) |
| NH-0' | 8.33 (s) |

TABLE 2

The observed $^{13}$C-NMR chemical shifts and signal multiplicity of Manumycin C, Manumycin D and Manumycin E in acetone-$d_6$ are summarized in the following Table.

| Carbon Position | Manumycin C $\delta^{13}$C (m) |
|---|---|
| 1 | 189.9 (s) |
| 2 | 129.2 (s) |
| 3 | 128.9 (d) |
| 4 | 71.9 (s) |
| 5 | 57.8 (d) |
| 6 | 53.4 (d) |
| 7 | 139.5 (d) |
| 8 | 131.4 (d) |
| 9 | 140.7 (d) |
| 10 | 132.2 (d) |
| 11 | 143.8 (d) |
| 12 | 122.9 (d) |
| 13 | 167.1 (s) |
| 1' | 165.6 (s) |
| 2' | 124.1 (d) |
| 3' | 142.8 (d) |
| 4' | 128.9 (d) |
| 5' | 141.4 (d) |
| 6' | 130.9 (d) |
| 7' | 140.6 (d) |
| 8' | 38.8 (t) |
| 9' | 31.4 (t) |
| 10' | 28.2 (d) |
| 11' | 22.6 (q) |
| 12' | 22.6 (q) |
| 13' | |
| 1" | 188.5 (s)* |
| 2" | 115.7 (s) |
| 3" | 172.9 (s)* |
| 4" | 26.0 (t) |
| 5" | 32.9 (t) |

*Signals were observed in a CDCl$_3$/Acetone-$d_6$ solvent mixture.

| Carbon Position | Manumycin D $\delta^{13}$C (m) |
|---|---|
| 1 | 190.0 (s) |
| 2 | 129.3 (s) |
| 3 | 128.2 (d) |
| 4 | 72.0 (s) |
| 5 | 57.9 (d) |
| 6 | 53.3 (d) |
| 7 | 139.6 (d) |
| 8 | 131.5 (d) |
| 9 | 140.8 (d) |
| 10 | 132.4 (d) |
| 11 | 143.9 (d) |
| 12 | 123.0 (d) |
| 13 | 167.2 (s) |
| 1' | 165.7 (s) |
| 2' | 124.1 (d) |
| 3' | 143.0 (d) |
| 4' | 129.3 (d) |
| 5' | 141.9 (d) |
| 6' | 128.7 (d) |
| 7' | 146.0 (d) |
| 8' | 41.9 (d) |
| 9' | 33.4 (t) |
| 10' | 26.8 (t) |
| 11' | 26.6 (t) |
| 12' | 26.8 (t) |
| 13' | 33.4 (t) |
| 1" | 188.5 (s)* |

TABLE 2-continued

The observed $^{13}$C-NMR chemical shifts and signal multiplicity of Manumycin C, Manumycin D and Manumycin E in acetone-$d_6$ are summarized in the following Table.

| | |
|---|---|
| 2" | 115.8 (s) |
| 3" | 172.9 (s)* |
| 4" | 26.1 (t) |
| 5" | 32.8 (t) |

| Carbon Position | Manumycin E $\delta^{13}$C (m) |
|---|---|
| 1 | 189.9 (s) |
| 2 | 129.2 (s) |
| 3 | 128.1 (d) |
| 4 | 71.9 (s) |
| 5 | 57.8 (d) |
| 6 | 53.4 (d) |
| 7 | 139.5 (d) |
| 8 | 131.4 (d) |
| 9 | 140.7 (d) |
| 10 | 132.2 (d) |
| 11 | 143.8 (d) |
| 12 | 122.9 (d) |
| 13 | 167.1 (s) |
| 1' | 165.6 (s) |
| 2' | 124.1 (d) |
| 3' | 142.8 (d) |
| 4' | 129.2 (d) |
| 5' | 141.6 (d) |
| 6' | 128.2 (d) |
| 7' | 147.1 (d) |
| 8' | 32.1 (d) |
| 9' | 22.3 (q) |
| 10' | 22.3 (q) |
| 11' | |
| 12' | |
| 13' | |
| 1" | 188.5 (s)* |
| 2" | 115.8 (s) |
| 3" | 172.9 (s)* |
| 4" | 26.0 (t) |
| 5" | 32.9 (t) |

EXAMPLE 2

Biological Activity

The biological activity of the present compounds was demonstrated as follows.

A) Determination of MIC against bacteria

To demonstrate their antimicrobial properties, the minimum inhibitory concentration (MIC) for each of the compounds Manumycin C, Manumycin D and Manumycin E of the invention was obtained against a variety of bacteria using a conventional broth dilution assay (serial broth dilution method using nutrient broth (Difco)). The results obtained are shown in Table 3 below, and demonstrate that Manumycins C, D and E have utility in treating bacterial infections.

TABLE 3

| | MIC (μg/ml) | | |
|---|---|---|---|
| Organism* | Manumycin C | Manumycin D | Manumycin E |
| Staphylococcus aureus A9537 | 2 | 1 | 8 |
| Staphylococcus aureus A9606 | 4 | 2 | 8 |
| Staphylococcus epi-dermidis A24548 | 2 | 1 | 8 |
| Bacillus subtilis A9506 | 1 | 0.5 | 8 |
| Salmonella typhimurium A27908 | 2 | 0.5 | 32 |
| Micrococcus luteus | 8 | 2 | 16 |

TABLE 3-continued

| Organism* | MIC (μg/ml) | | |
|---|---|---|---|
| | Manumycin C | Manumycin D | Manumycin E |
| A9852 | | | |
| *M. luteus* A21349 | 4 | 1 | 16 |
| *Escherichia coli* SGB888 | 0.32 | 0.1 | 2.5 |
| *Proteus mirabilis* A9900 | 128 | 128 | 128 |
| *Klebsiella pnneumoniae* A9664 | 128 | 128 | 128 |
| *Enterobacter cloacae* A9656 | 128 | 128 | 128 |
| *Pseudomonas aeruginosa* A9843 | 64 | 128 | 128 |

*Numbers following genus and species of microorganism denote specific strains.

B) Inhibition of Farnesylation of Ras Protein p21

Employing the assay described by Manne et al., "Identification and preliminary characterization of protein-cysteine farnesyltransferase", *Proc. Natl. Acad. Sci. USA*, 87:7541-7545 (1990), Manumycin C was found to have an $IC_{50}$ value of 100 μM in inhibiting the farnesylation of Ras protein p21. The $IC_{50}$ value of Manumycin D in this system was 92.5 μM; that of Manumycin E was 120 μM.

What is claimed is:

1. A compound which is Manumycin C, having a stereoisomeric form corresponding to that produced by Streptomyces sp. A.T.C.C. No. 55484. oxidized Manumycin C having said stereoisomeric form, or a salt or prodrug thereof.

2. A compound of claim 1 which is Manumycin C or a salt thereof.

3. A compound of claim 1 which is oxidized Manumycin C or a salt thereof.

4. A pharmaceutical composition, comprising a physiologically tolerated compound of claim 1 and a physiologically tolerated vehicle or diluent.

5. A composition for the inhibition of bacterial growth, comprising a compound of claim 1 which is Manumycin C, oxidized Manumycin C, or a salt thereof, in an mount effective therefor, and a vehicle or diluent.

6. A compound of claim 1 which is pure or substantially pure.

7. A compound which is Manumycin E, having a stereoisomeric form corresponding to that produced by Streptomyces sp. A.T.C.C. No. 55484. oxidized Manumycin E having said stereoisomeric form, or a salt or prodrug thereof.

8. A compound of claim 7 which is Manumycin E or a salt thereof.

9. A compound of claim 7 which is oxidized Manumycin E or a salt thereof.

10. A pharmaceutical composition, comprising a physiologically tolerated compound of claim 7 and a physiologically tolerated vehicle or diluent.

11. A composition for the inhibition of bacterial growth, comprising a compound of claim 7 which is Manumycin E, oxidized Manumycin E, or a salt thereof, in an amount effective therefor, and a vehicle or diluent.

12. A compound of claim 7 which is pure or substantially pure.

* * * * *

UNITED STATES PATENT AND TRADEMARK OFFICE
CERTIFICATE OF CORRECTION

PATENT NO. : 5,444,087

DATED : August 22, 1995

INVENTOR(S) : Pramathesh S. Patel and Yue-Zhong Shu

It is certified that error appears in the above-identified patent and that said Letters Patent is hereby corrected as shown below:

Column 13, line 32, after "55484" the period "." should be a comma --,--.

Column 14, line 11, "mount" should read --amount--.

Column 14, line 17, after "55484" the period "." should be a comma --,--.

Signed and Sealed this

Twenty-eighth Day of November 1995

Attest:

BRUCE LEHMAN

*Attesting Officer*   *Commissioner of Patents and Trademarks*